United States Patent [19]
Kim et al.

[11] Patent Number: 5,773,468
[45] Date of Patent: Jun. 30, 1998

[54] IRREVERSIBLE HIV PROTEASE INHIBITOR HAVING AN ANTI-AIDS ACTIVITY AND PROCESS FOR THE PREPARATION THEREOF

[75] Inventors: Sung Chun Kim; Young Chan Son; Ho Il Choi; Heungsik Yoon; Chi Hyo Park; Nakyen Choy; Chang Sun Lee, all of Daejeon; Jong Sung Koh, Seoul; Kwang Yul Moon, Daejeon; Won Hee Jung, Daejeon; Chung Ryeol Kim, Daejeon, all of Rep. of Korea

[73] Assignee: LG Chemical Limited, Seoul, Rep. of Korea

[21] Appl. No.: 572,402

[22] Filed: Dec. 14, 1995

Related U.S. Application Data

[63] Continuation-in-part of Ser. No. 473,877, Jun. 7, 1995, which is a continuation-in-part of Ser. No. 341,352, Nov. 17, 1994, which is a continuation-in-part of Ser. No. 159,382, Nov. 30, 1993.

[30] Foreign Application Priority Data

Oct. 26, 1995 [KR] Rep. of Korea ...................... 95-37292

[51] Int. Cl.$^6$ .......................... A01N 43/20; A01N 31/34
[52] U.S. Cl. .......................... 514/475; 549/552; 549/523
[58] Field of Search ............................ 574/475; 549/552, 549/523

[56] References Cited

PUBLICATIONS

Henderson et al., J. Virol., 62, 2597, Feb. 1988.
Moelling et al., FEBS Letter, 261, 373, Apr. 1990.
Pal et al., Proc. Natl. Aca. Sci., 85, 9283, Jun. 1988.
Grant et al., Bioorg. Med. Chem Letter, 2, 1441, Mar. 1992.

*Primary Examiner*—Charles T. Jordan
*Assistant Examiner*—Anthony R. Chi
*Attorney, Agent, or Firm*—Anderson Kill & Olick, P.C.

[57] ABSTRACT

The present invention relates to a novel compound of formula (I) and pharmaceutically acceptable salts, hydrates and solvates thereof which is an irreversible HIV protease inhibitor; a process for the preparation thereof; and a pharmaceutical composition containing the compound as an active ingredient which is useful for treating or preventing diseases caused by HIV infection.

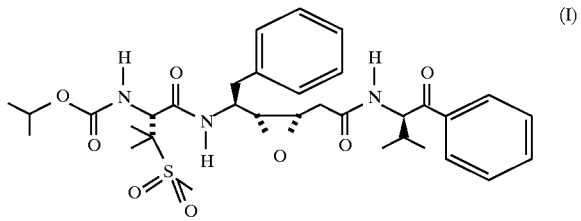

3 Claims, No Drawings

IRREVERSIBLE HIV PROTEASE INHIBITOR HAVING AN ANTI-AIDS ACTIVITY AND PROCESS FOR THE PREPARATION THEREOF

CROSS REFERENCE TO RELATED APPLICATION

This application is a continuation-in-part application of copending U.S. Ser. No. 08/473,877 filed on Jun. 7, 1995, which is a continuation-in-part application of copending U.S. Ser. No. 08/341,352 filed on Nov. 17, 1994, which is, in turn, a continuation-in-part application of copending U.S. Ser. No. 08/159,382 filed on Nov. 30, 1993.

FIELD OF THE INVENTION

The present invention relates to a novel compound for inhibiting human immunodeficiency virus ("HIV") protease, process for the preparation thereof, and a pharmaceutical composition, containing the compound as an active ingredient, for treating or preventing AIDS resulted from HIV infection.

BACKGROUND OF THE INVENTION

HIV which is known to cause AIDS(acquired immunodeficiency syndrome) is one of retroviruses which contain their genetic information in RNA; and consists of a core, envelope proteins, a lipid membrane and glycoproteins. The HIV core comprising two single stranded RNA and reverse transcriptase is enclosed by envelope proteins, which are in turn enclosed by a lipid membrane. Glycoproteins located on the outside of the lipid membrane consist of gp120 and gp40 of which gp120 plays a major role in recognizing and infecting T cells.

Similar to other retroviruses, HIV is unusual in that its growth cycle has a stage in which the flow of information is reversed(that is, RNA→DNA) contrary to the usual mechanism (DNA→RNA).

For such a reverse mechanism, the existence of a reverse transcriptase which makes double-stranded DNA from a single-straded RNA template is essential; and, consequently, only retroviruses have a reverse transcriptase.

Accordingly, it has been predicted that HIV can be incapacitated by way of inhibiting the activity of the reverse transcriptase; and, hereto, many reverse transcriptase inhibitors have been developed. Such inhibitors include: azidothymidine (AZT) developed by Burrows-Wellcome Co.; 2,3-deoxyinosine(DDI) of Bristol Meyers Squibb Co.; 2,3'-dideoxycytosine(DDC) of Hoffmann-La Roche AG; D4T of Glaxo Co. and the like.

However, the above and other compounds known in the art as agents for AIDS treatment have shown a rather limited effect of prolonging patients, life, because they are effective against virus infection of intact cells, but not against replication of viruses in infected cells. Further, they tend to cause serious side effects such as decrease of the number of blood platelets, cytopenia in marrow, and the like. Besides, a number of viruses having tolerance against the above compounds have been found.

Another important enzyme which is active during HIV replication is HIV protease responsible for the proteolytic processing of proprotein precursors. Gag-protein(p55) or gag-pol protein(p165) are processed into structural envelope proteins and essential functional proteins for HIV replication such as protease, reverse transcriptase and integrase(see Henderson et al., *J. Virol.*, 62, 2587(1988)). Accordingly, HIV protease Inhibitors have been also considered as a potential AIDS treating agent.

HIV protease is present in a dimeric form having a $C_2$ symmetry; and, each monomer has a molecular weight of 10,793 daltons and consists of 99 amino acids. HIV protease is classified as an aspartic protease since it is proved to have the typical sequence of Asp-Thr-Gly at the active site, and can be inhibited by pepstatin, a known inhibitor of aspartic proteases. Pepstatin has a hydroxyethyl group instead of a peptide bond at the site where reaction with a protease occurs, which is similar to the form of a transition state during the protease reaction; and, it appears that the form having a hydroxyethyl group binds to a protease more strongly than a polypeptide having a peptide bond; and therefore, pepstatin prohibits a protease reaction.

In this connection, recent studies on HIV protease Inhibitors have been focused on the development of compounds similar to the transition state which has a high affinity to the protease(see Roberts et al., *Science*, 248, 358(1990); Signal et al., EP Publication No. 0337714; Handa et al., EP Publication No. 0346847; Desolms et al., EP Publication No. 0356223; Dreyer et al., EP Publication No. 0352000; Signal et al., EP Publication No. 0357332; Hanko et al., EP Publication No. 0361341; Bone et al, *J. Am. Chem. Soc.*, 113, 9382(1991); and Urban et al., *FEBS Letter*, 298, 9(1992)).

These compounds, however, suffer from the fact that they are reversible inhibitors. Because irreversible inhibitors could block the protease activity permanently and would thus be more desirable, efforts have been made for the development of irreversible inhibitors by way of introducing an epoxide group to the reaction site thereof (see Moelling et al., *FEBS Letter*, 261, 373(1990); Pal et al., *Proc. Natl. Aca. Sci.*, 85, 9283(1988); Grant et al., *Bioorq. Med. Chem. Letter*, 2, 1441(1992); and EP Publication No. 0492136A).

SUMMARY OF THE INVENTION

Accordingly, it is a primary object of the present invention to provide an irreversible HIV protease inhibitor having a high inhibitory effect against HIV protease, useful for the treatment of AIDS.

Another object of the present invention is to provide a process for preparing the inhibitor.

A further object of the present invention is to provide a pharmaceutical composition containing the inhibitor in a therapeutically effective amount as an active ingredient, and pharmaceutically acceptable carriers, which is effective in treating or preventing AIDS or HIV infection.

In accordance with the present invention, there are provided a novel cis-epoxide compound of formula (I) which contains functionalized amino groups, and its pharmaceutically acceptable salts, hydrates and solvates thereof:

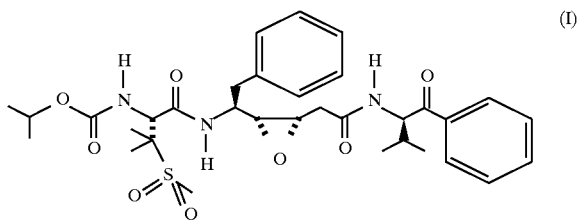

(I)

DETAILED DESCRIPTION OF THE INVENTION

The compound of the present invention has form asymmetric carbons; and, therefore, the present invention encompasses, within its scope, racemic mixtures as well as mixtures of diastereomers of the compound of the invention and pharmaceutically acceptable salts, hydrates and solvates thereof.
The cis-epoxide compound of formula (I) of the present invention may be prepared as illustrated in the following Scheme 1.
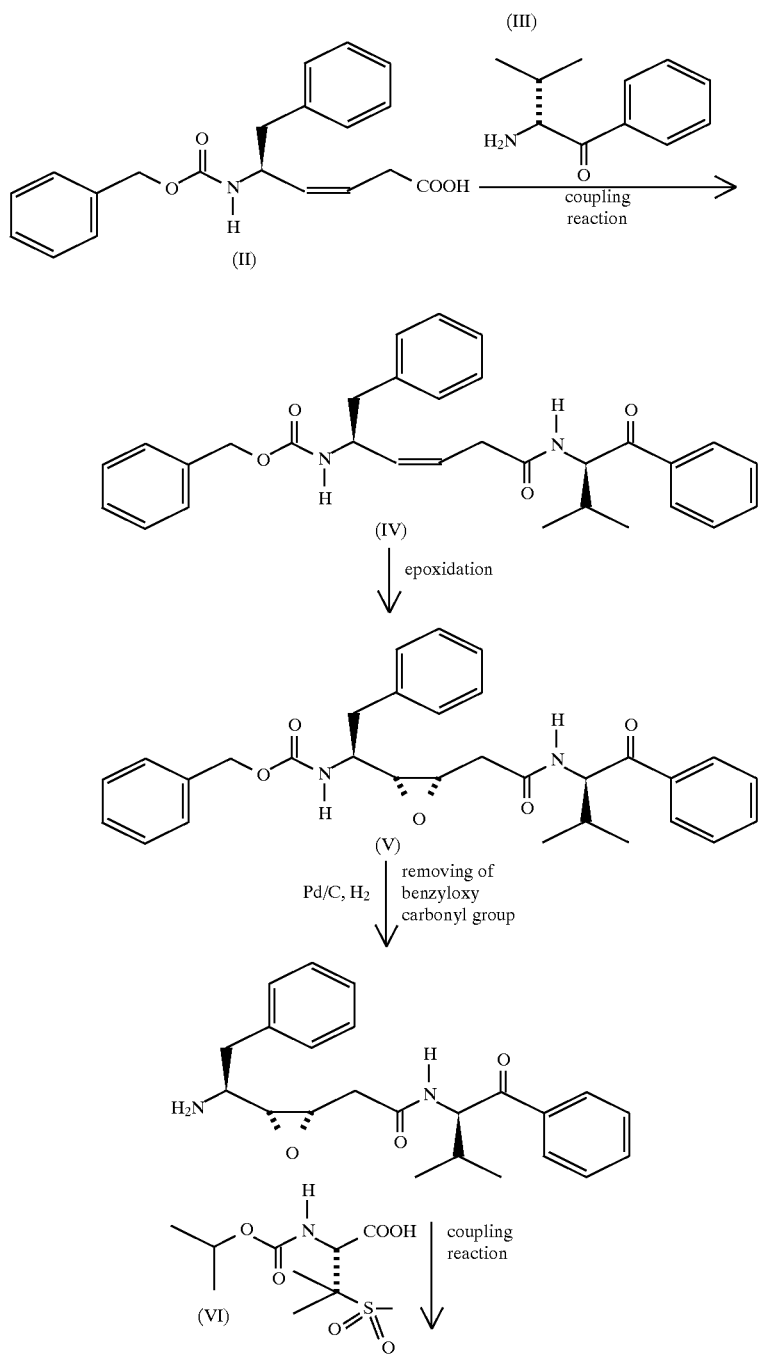

-continued
Scheme 1

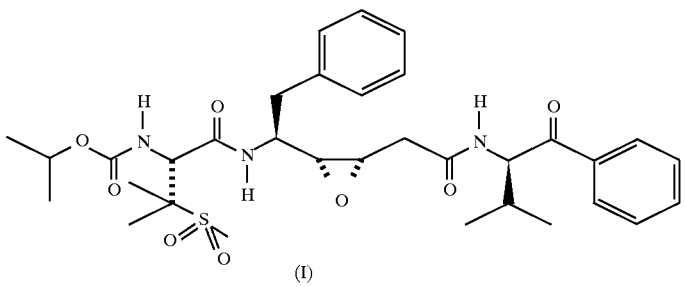

(I)

As shown in Scheme 1, a coupling reaction of a compound of formula (II) with a compound of formula (III) is carried out to give a compound of formula (IV); the compound of formula (IV) is epoxidized to give a compound of formula (V); and after the removing the benzyloxycarbonyl protecting group from the compound of formula(V) to obtain a compound having a deprotected amino group, another coupling reaction of the compound having the deprotected amino group with a compound of formula (VI) is carried out to give the desired compound of formula (I).

The coupling reagents which can be used for the above coupling reactions in Scheme 1 may include, but are not limited to, dicyclohexyl carbodiimide(DCC), 3-ethyl-3'-(dimethylamino)-propylcarbodiimide(EDC), bis-(2-oxo-3-oxazolidinyl chlori-de(BOP-Cl), diphenylphosphoryl-azide (DPPA), and the like.

Alternatively, the coupling reactions may be carried out without any coupling reagent by employing acyl halides or activated ester derivatives. Suitable acyl halides include acyl chlorides; and, suitable activated ester derivatives are those commonly used for activating a carboxylic acid groups for coupling with an amine to form an amide bond, or for coupling with an alcohol to form an ester bond: these include, but not limited to, derivatives obtained using alkoxycarbonyl chlorides such as methoxycarbonyl chloride and isobutoxycarbonyl chloride; carboxylic acid anhydrides; and other compounds such as N-hydroxybenzotriazole, N-hydroxyphthalimide, N-hydroxysuccinimide, N-hydroxy-5-norbornene-2,3-clicarbox-amide and 2,4,5-trichlorophenol.

The epoxidation reaction in the above Scheme 1 can be carried out in accordance with a known method by employing metachloroperoxybenzoic acid.

The removal of benzyloxycarbonyl protecting group may be carried out in accordance with a known method in the art, for instance, conducting a hydrogenolysis reaction in the presence of a Pd/C catalyst under a hydrogen atmosphere.

The compound of formula (II) can be prepared in accordance with the procedure of EP Publication No. 0601486 A1, which is a modified version of the method described in Keinan et al., *Tetrahedron*, 47, 4631–4638(1991); and Corey & Shimaji, *J. Am. Chem. Soc.*, 105, 1662–1664(1983).

The functionalized amine (III)(which provides an N-terminal group) may be prepared in accordance with the procedure shown in Scheme 2.

Scheme 2

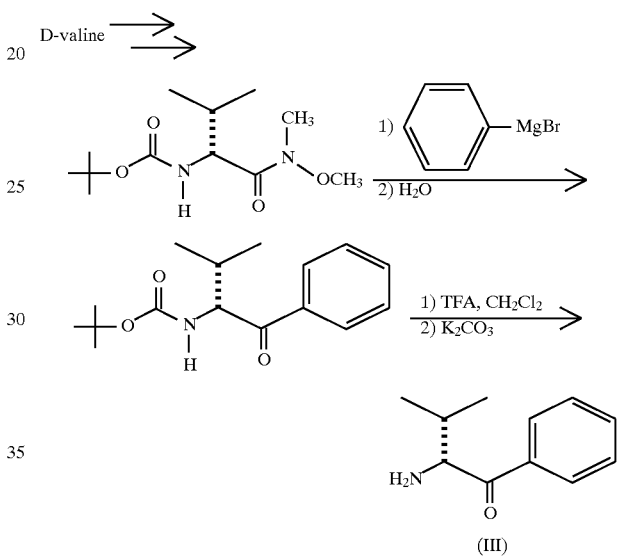

As shown in Scheme 2, the N,O-dimethylamide derivatives prepared in accordance with the procedure described in Weinreb et al, *Tetrahedron Lett.*, 22, 3815(1981) is subjected to a Grignard reaction, followed by removal of the protecting group to obtain the desired compound of formula(III).

The functionalized carboxylic acid(VI)(which provides a C-terminal group) may be prepared in accordance with the procedure shown in Scheme 3.

Scheme 3

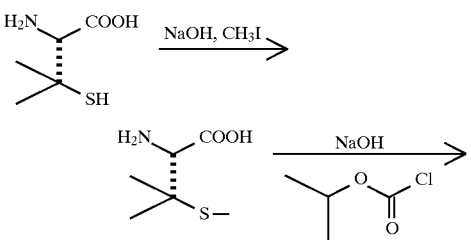

-continued
Scheme 3

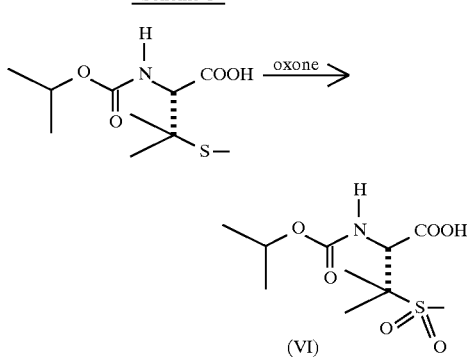

As shown in Scheme 3, after methylating the mercapto group of L-penicillamine, the amino group of the methylated compound is protected with isopropylchloroformate and the protected compound is reacted with oxone to obtain the desired compound of Jormula(VI).

The compound of the present invention may be used for the treatment or prophylaxis of diseases caused by HIV, including AIDS. Accordingly, the present invention includes pharmaceutical compositions which contain, in addition to the compound of the invention, non-toxic, inert pharmaceutically suitable carriers. In general, it is advantageous both in human and veterinary medicine to administer the active compound of the invention in total amounts of about 5 to 30 mg/kg of body weight Every 24 hours, if appropriate, in the form of several individual dosages, to achieve desired results. However, it may be necessary to adjust the above dosage depending on the body weight and other particulars of the subject to be treated, the symptom and severity of the disease, the type of formulation and the particular methods of administrating the medicament.

The composition of the present invention may be administered orally or by injection. These compositions may be in the form of tablets, capsules, pills, powders, granules, solutions, emulsions, suspensions and the like.

Solutions, emulsions and suspensions may be prepared by using conventional methods. Solutions and emulsions may contain, in addition to the active compound of the invention, customary carriers or excipients, such as solvents, solubilizing agents and emulsifiers, for example, water, ethyl alcohol, isopropyl alcohol, propylene glycol and oils. Suspensions can contain, in addition to the active compound, customary carriers or excipients, such as liquid diluents(e.g.: water, ethyl alcohol or propylene glycol) and suspending agents(e.g.: ethoxylated isostearyl alcohol, polyoxyethylene sorbitol and sorbitan esters), microcrystalline cellulose and aluminum metahydroxide, or mixtures thereof.

Solid compositions for oral administration are preferably in the form of capsules and enteric coated tablets in consideration of the chemical characteristics of the compound; and may include an inert diluent such as sucrose, lactose, etc. and a lubricant such as magnesium stearate. The compound of the present invention may be administered simultaneously with one or more other anti-AIDS agents or immunomodulators.

The formulations of the present invention are not limited to those described above, but can be any form which is useful for treating and preventing disease caused by the HIV infection.

The following Preparation Examples and Examples are provided for purposes of illustrating certain aspects of the present invention only; and are not to be construed as limiting the scope of the present invention in any way.

The terms and abbreviations used in the Examples have their normal meaning unless otherwise designated, for example, "° C." refers to degrees Celsius; "N" refers to normal or normality; "mmol" refers to millimole; "g" refers to gram; "ml" means milliliter; "M" refers to molar; "NMR" refers to nuclear magnetic resonance; and "FABMS" refers to fast atomic bombardment mass spectrometry.

Unless otherwise specified, percentages or ratios given below for solids in solid mixtures, liquids in liquids and solids in liquids are on a w/w, v/v and w/v basis, respectively.

PREPARATION EXAMPLE 1

Preparation of (S)-5-[(N-benzyloxy-carbonyl)amino]-6-phenyl-hex-3-(cis)-ene-1-carboxylic acid (Compound of formula(II))

1-1) Preparation of 5-L-(N-benzyloxycarbonyl)amino-6-phenyl-hex-3-(cis)-enyl-4'-methyl-2',6',7'-trioxa-bicyclo-[2',2',2'] oxetane 60.89 g(0.12 mol) of 1-(2-triphenylphosphonium-methyl)-4'-methyl-2',6',7'-trioxa-bicyclo[2',2',2']oxetane bromide prepared according to the method described by Keinan et al. in Tetrahedron, 26, 4631–4638(1991) was dissolved in 400 ml of tetrahydrofuran and the mixture was stirred at −78° C. Then, 220 ml(0.11 mol) of 0.5M potassium hexamethyldisilazane was added thereto and the whole mixture was stirred at −78° C. for 1 hour. To this mixture was added, slowly over 20 minutes, a solution of 30 g(0.106 mol) of L-(N-benzyloxycarbonyl)phenylalaninal in 150 ml of tetrahydrofuran maintained at −78° C.; then the whole mixture was stirred at −78 C. for 1 hour and subsequently at room temperature for 1 hour; and then, the reaction was quenched by adding water. After removing the solvent from the reaction mixture, the residue was dissolved in ethylacetate and washed with a saturated $NaHCO_3$ solution and with water. The organic layer was dried over anhydrous $MgSO_4$ and the residue was subjected to column chromatography using hexane:ethyl acetate:triethylamine (70:30:5) as an eluent to obtain 36.5 g of the title compound (yield: 84%).

$^1$H NMR(CDCl$_3$) δ 0.8(s, 3H), 2.2–3.0(m, 4H), 3.9(s, 6H), 4.6(m, 1H), 4.8(br, 1H), 5.05(s, 2H), 5.4–5.6(m, 2H), 7.1–7.5(m, 10H); [α]$_D$=+25.2(c=0.50, methanol)

1-2) Preparation of (S)-5-L-(N-benzyloxycarbonyl)amino-6-phenyl-hex-3-(cis)-ene-1-carboxylic acid 2.5 g(6 mmol) of the compound obtained in Preparation Example 1-1) was dissolved in a mixture of water and t-butanol containing 1% or less of conc. hydrochloric acid, and the resulting solution was refluxed for 20 hours. The solvent was distilled off under a reduced pressure and the residue, after adjusting its pH to above 9 with a saturated $K_2Co_3$ solution, was washed with ethyLacetate. The aqueous layer was then adjusted to pH 2, extracted with ethyl acetate, and the organic layer was dried cover anhydrous $MgSO_4$. On removing the solvent 1.62 g of the title compound was obtained(yield: 80%).

¹H NMR(CDCl₃) δ 2.7–3.3(m, 4H), 4.6(m, 1H), 4.8(br, 1H), 5.05(s, 2H), 5.4(t, 1H), 5.6(m, 1H), 7.1–7.5 (m, 10H); Mass(FAB, m/e) 340(M+1)

PREPARATION EXAMPLE 2

Preparation of (2S)-1-phenyl-3-methyl-2-amino-1-butanone (Compound of formula(III))

2-1) Preparation of (2S)-[(N-t-butoxycarbonyl)amino]-1-phenyl-3-methyl-1-butanone 9.2 g(37.4 mmole) of N-t-butoxycarbonyl-N'-methoxy-N'-methyl-D-valine amide was dissolved in 120 ml of anhydride tetrahydrofuran and 56.1 ml(112.2 mmole) of 2M phenylmagnesium chloride solution in tetrahydrofuran.was added thereto at 0° C. The mixture was stirred at room temperature for 12 hours and then, the reaction was quenched by adding water at 0° C. The solvent was removed by distillation under a reduced pressure and the residue was extracted with 600 ml of methylene chloride. The organic layer was washed with ammonium chloride solution (3×400 ml) and dried over anhydrous MgSO₄. After removing the solvent under a reduced pressure, the residue was subjected to column chromatography using hexane:ethyl acetate(9:1) as an eluent to obtain 7.5 g of the title compound (yield: 72%).

¹H NMR(CDCl₃) δ 0.85(d, 3H), 1.11(d, 3H), 1.55(s, 9H), 2.23(m, 1H), 5.31(m, 1H), 5.50(m, 1H), 7.51–8.12(m, 5H)

2-2) Preparation of (2S)-1-phenyl-3-methyl-2-amino-1-butanone 7.5 g of the compound obtained in Preparation Example 2-1) was dissolved in 200 ml of dichloromethane and 100 ml of trifLuoroacetic acid was added thereto, and the mixture was stirred for 12 hours at room temperature. The solvent was distilled off under a reduced pressure and 100 ml of water and 100 ml of ether were added to the residue. The organic layer containing impurities was discarded, and then, 150 ml of ethyl aicetate was added to the aqueous layer and the pH of the mixture was adjusted to above 12 with a saturated potassium carbonate. Finally, 3.8 g of the title compound was isolated from the ethyl acetate solution (yield: 79%).

¹H NMR(CDCl₃) δ 0.78(d, 3H), 1.10(d, 3H), 1.72(s, 2H), 2.15(m, 1H), 4.33(d, 1H), 7.50–7.91(m, 5H)

PREPARATION EXAMPLE 3

Preparation of [(5S)-[(N-benzyloxy-carbonyl)amino]]-6-phenyl-3-(cis)-ene-1-hexanoyl]-[(2S)-(1-phenyl-3-methyl-1-oxo)butylamino]amide (Compound of formula (IV))

1.2 equivalents of each of EDC, N-hydroxylbenzotriazole HOBT) and triethylamine were added to 5.35 g(15.8 mmol) of the product obtained in Preparation Example 2 and the mixture was dissolved in 150 ml of dimethylformamide. Then, 2.8 g(15.8 mmol) of the product obtained in Preparation Example 1 was added to the solution at 0° C. and the whole mixture was stirred at room temperature for 16 hours. The solvent was distilled off under a reduced pressure and the residue was dissolved in ethyl acetate and washed with a saturated NaHCO₃ solution. The organic layer was dried over anhydrous MgSO₄ and distilled under a reduced pressure to remove solvent. The residue was then subjected to column chromatography using ethyl acetate:hexane(1:4) as an eluent to obtain 6.4 g of the title compound(yield: 77%).

¹H NMR(CDCl₃) δ 0.85(d, 3H), 1.04(d, 3H), 2.24(m, 1H), 2.81–2.99(m, 4H), 3.75(m, 1H), 5.01(m, 1H), 5.13(m, 2H), 5.45(t, 1H), 5.59(m, 1H), 5.69(m, 1H), 7.01(m, 1H), 7.17–8.01(m, 15H)

PREPARATION EXAMPLE 4

Preparation of [(5S)-[(N-benzyloxy-carbonyl)amino]-(4R,3S)-epoxy-6-phenyl-1-hexanoyl]-[(2S)-(l-phenyl-3-methyl-l-oxo)butylamino]amide (Compound of formula (V))

3.1 g(6.22 mmol) of the compound obtained in Preparation Example 3 was dissolved in 150 ml of dichloromethane and 2 equivalents of metachloroperoxybenzoic acid was added thereto; then stirred for 18 hours at room temperature. 100 ml of 10% Na₂S₂O₃ solution was added and the mixture was stirred for 30 minutes. The organic layer was washed with a saturated NaHCO₃ solution and dried over anhydrous MgSO₄. On removing the solvent, 2.5 g of the title compound was obtained(yield: 80%).

¹H NMR(CDCl₃) δ 0.75(d, 3H), 1.02(d, 3H), 2.01(m, 1H), 2.14–2.40(m, 2H), 2.82–3.15(m, 3H), 3.31(m, 1H), 3.80(m, 1H), 5.05(d, 1H), 5.13(s, 2H), 5.61(s, 2H), 5.61(m, 1H), 6.61(d, 1H), 7.15–8.00(m, 15H)

PREPARATION EXAMPLE 5

Preparation of N-isopropyloxycarbonyl-β-methanesulfonyl-L-valine (Compound of formula (VI))

4-1) Preparation of N-isopropyloxycarbonyl-β-(S-mehyl)-L-valine 4.5 g(30 mmol) of β-mercapto-L-valine was added to a mixture of 60 ml of dioxane and 20 ml of water and cooled to 0° C. To the Mixture, 10 ml of 6N sodium hydroxide was added to dissolve the solid compound. 4.62 g(33 mmol) of methyl iodide was added to the solution and reacted at 0° C. for 3 hours and subsequently at room temperature for 2 hours. The reaction mixture was cooled to 0° C. and 5 ml of 6N sodium hydroxide and 40 ml of 1M isopropylchloroformate in toluene were added slowly. The resultant mixture was stirred at 0° C. for 1 hour and subsequently at room temperature for 2 hours and then the reaction was quenched. The solvent was removed from the reaction mixture by distillation under a reduced pressure and 50 ml of water and 50 ml of ether were added to the residue and the organic layer containing unreacted isopropyl-chloroformate was discarded. 10 ml of ethyl acetate was added to the aqueous layer and the pH of the mixture was adjusted to below 3 with 6N HCl. The organic layer was separated, dried over anhydrous MgSO₄, and the solvent was distilled off under a reduced pressure to give 5.5 g of the title compound(yield: 73%).

¹H NMR(CDC₃) δ 1.30(s, 6H), 1.48(s, 6H), 2.13(s, 6H), 4.41(m, 1H), 4.99(m, 1H), 5.61(m, 1H), 8.50(br, 1H)

5-2) Preparation of N-isopropyloxycarbonyl-β-methanesulfonyl-L-valine 5.5 g(22 mmol) of the compound obtained in Preparation Example 5-1) was dissolved in 150 ml of methanol and the solution was cooled to 0° C. 3 equivalents of oxone was added to the methanol solution and reacted for 3 hours. After the completion of the reaction, solvent was removed by distillation under a reduced pressure and 200 ml of ethylacetate and 100 ml of water were added to the residue. The organic layer was separated, dried over anhydrous MgSO$_4$ and the solvent was removed by distillation under a reduced pressure to give 5.7 g of the title compound(yield: 92%).

$^1$H NMR(CDCl3) δ 6 1.27(m, 6H), 1.53(s, 3H), 1.61(s, 3H), 2.99(s, 3H), 3.61–3.92(br, 1H), 4.72(m, 1H), 4.98(m, 1H), 5.97(br, 1H)

EXAMPLE

Preparation of [(5S)-[(N-isopropyloxycarbonyl)-β-methanesulfonyl-L-valinyl]amino]-(4R,3S)-epoxy-6-phenyl-l-hexanoyl]-[(2S)-(1-phenyl-3-methyl-1-oxo)butylamino]amide (Compound of formula (I))

200 mg(0.39 mmol) of the compound obtained in Preparation Example 4 was dissolved in 20 ml of methanol and 10 mg of 10% Pd/C was added thereto. The reaction mixture was stirred at room temperature under a hydrogen atmosphere for 2 hours. The resulting solution was filtered through Celite to remove inorganic catalysts. The solvent was removed by distillation under a reduced pressure to obtain an amine compound free of the benzyloxy carbonyl protecting group.

110 mg(0.39 mmol) of the compound obtained in Preparation Example 5 was dissolved in 500 ml of dimethylformamide and 1 equivalent of 4-methylmorphorin(39 mg) was added thereto. The resultant mixture was cooled to –20° C., 1 equivalent of isobutylchloroformate(52 mg) was added thereto, and stirred for 30 minutes and cooled to –78° C. To this mixture was added 1 equivalent(150 mg) of the above amine compound dissolved in 5 ml of dichloromethane. The whole mixture was warmed to 25° C. for 2 hours, and stirred for 1 hour. The reaction was quenched by adding water and resulting solution was diluted with dichloromethane and washed with saturated NaHCO$_3$ solution. The organic layer was dried over anhydrous MgSO$_4$ and the solvent was distilled off under a reduced pressure. The residue was subjected to column chromatography using ethyl acetate-:hexane (6:4) as an eluent to obtain 125 mg of the title compound(yield: 55%).

$^1$H NMR(CDCl$_3$) δ 0.85(d, 3H), 1.02(d, 3H), 1.25(m, 6H), 1.50 (s, 3H), 1.58(s, 3H), 2.11(m, 1H), 2.21(m, 1H), 2.35(m, 1H), 2.92(s, 3H), 2.99–3.12(m, 3H), 3.32(m, 1H), 4.15(m, 1H), 4.62(d, 1H), 4.95 (m, 1H), 5.58(m, 1H), 5.90(d, 1H), 6.75(d, 1H), 7.05(d, 1H), 7.20–8.00(m, 10H)

Assay for Inhibitory Effect on HIV Protease

The inhibitory effect on HIV protease of the compound of the present invention was determined by the following procedure.

To a buffer solution comprising 50 mM sodium acetate, pH 5.5, 1mM dithiothreitol(DTT), 1 mM ethylenediaminetetraacetate (EDTA), 75M ammonium sulfate and 0.1% NP40(NONIDET P-40; Sigma Chemical Co., U.S.A.), was added a pre-determined amount of the compound obtained in Example to prepare a preincubation solution having a known concentration of the compound. The inhibition reaction was initiated by adding 2.6 nM of HIV-1 protease to the preincubation solution. 10 μl samples of the reaction solution were taken at a given time interval and each sample was added to 80 μl of assay solution containing 100 μM of reaction substrate in the same buffer solution as above to assay for the residual enzyme activity. In this step, an oligopeptide consisting of 11 amino acids, i.e., NH$_2$-Ser-Ile-Ala-Glu-(p-NO$_2$)-Phe-Leu-Val-Arg-Ala-Lys-His-H, was used as a reaction substrate. This oligopeptide undergoes cleavage at the amide bond between (P-NO$_2$)-Phe and Leu upon the HIV protease attack. The reaction rate was determined by subjecting both the substrate before the reaction and the product after the reaction to HPLC separation and then measuring the amount of the product relative to the substrate, using the strong absorbance of (p-NO$_2$)-Phe at 280 nm. The decrease in the enzyme activity with time was measured for each sample and the natural logarithmic values (ln) of the data points in a given experiment were plotted against time to obtain a linear correlation line. k$_{obs}$ was then calculated from the slope of the line.

The inhibition constant was calculated according to the following equation:

$$\frac{1}{k_{obs}} = \frac{1}{k_{ina}} + \frac{K_I}{k_{ina}} \cdot \frac{1}{[I]}$$

wherein:

K$_{obs}$ is a rate constant representing the rate of decrease in enzyme activity in the presence of the inhibitor, K$_{ina}$ is a rate constant representing the rate of the irreversible covalent bond formation between the enzyme and the inhibitor (in Michaelis-Menten complex), K$_I$ is an inhibition constant represented by the equilibrium constant for the formation of the Michaelis-Menten complex from an enzyme and an inhibitor, and

[I] designates the inhibitor concentration.

The above equation is applicable to an experiment carried out under the condition in which the concentration of inhibitor is far higher than that of enzyme(Steady State Kinetic). In case when the experiment was carried out under the condition in which the concentration of the inhibitor was comparable to that of the enzyme, as was the case when the inhibitor activity was very high, the reaction sequence of

(wherein, E, I, EI and EI' stand for an enzyme, an inhibitor, a Michaelis-Menten complex and a complex having covalent bond formed between the enzyme and the inhibitor, respectively; and K$_1$ and k$_{ina}$ have the same meanings as defined above) was directly analyzed to calculate the relative concentration of active enzyme, i.e., [E]/([E]+[EI]+[EI']) at a given time. The inhibition constants K$_I$, the rate constant k$_{ina}$ and the second order rate constant k$_{ina}$/K$_I$ were tabulated by inputting the value of [E]/([E]+[EI]+[EI']) into KINSIM/FITSIM program. The K$_I$, k$_{ina}$ and k$_{ina}$/K$_I$ values obtained in the above assay for the compound of the present invention were 12 nM, 3.2 min$^{-1}$, and 2.7×10$^7$ min$^{31}$ $^1$M$^{-1}$, respectively. In contrast, MK-639, the reversible protease inhibitor of Merck Co., had a K$_I$ value of 0.38 nM.

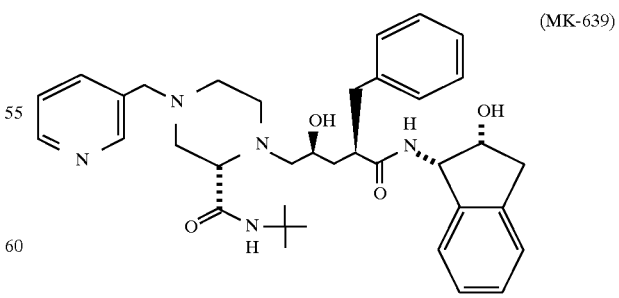

Determination of anti-viral activity and cytotoxicity

The anti-viral activity of the compound of the present invention was determined by measuring the concentration of the compounds at which the proliferation of HIV is inhibited by 50%(IC$_{50}$)

1×10⁵ cells of each of H9(ATCC HTB 176) and Sup T1 cell lines were added to the wells of a 24-well microtiter plate and the compound of the present invention was added thereto in various concentrations. 200 TCID$_{50}$(200-fold of 50% tissue culture infection dose) of HIV-1 inoculum and rpmi-1640 medium(Sigma Chemical Co., U.S.A) were added successively to the wells and the plate was incubated at 37° C. In case of Sup T1, the number of syncytium formed was investigated after 3 to 9 days. IC$_{50}$ of the compound was determined by measuring the concentration of the inhibitor at which the number of syncytium becomes 50% of that formed under the same condition without the inhibitor.

In the case of H9, three-quarters(¾) of the culture medium was refreshed every 3 days. After 9 days, 6 ml of the culture fluid was centrifuged at 1000 rpm for 10 minutes. To 5 ml of the resulting supernatant were added 2.5 ml of 30% polyethylene glycol(PEG, M.W. 6000–8000) and 0.4M NaCl. The resulting solution was allowed to stand at 0° C. overnight to precipitate virus particles. The solution was centrifuged at 2000 rpm for 45 minutes, the supernatant was discarded therefrom and the precipitate was diluted with 20 ml of a reverse transcriptase suspension buffer(50 mM tris-HCl(Sigma), pH 7.5, 1 mM dithiothreitol, 20% glycerol, 0.25M KCl and 0.25% Triton X-100). The resulting suspension was stored in an Effendorf tube at −70° C. until use. A cycle of freezing the above virus suspension for 2 minutes in dry ice and thawing it at 37° C. for 2 minutes was repeated three times and the resulting suspension was centrifuged et 4° C. The resulting supernatant was used in carrying out the reverse transcriptase assay.

10 μl of the above virus suspension was added to a solution prepared by mixing: 10 μl of buffer solution(250 mM tris-HCl, pH 7.5, 37.5 mM MgCl$_2$, 0.25% triton X-100), 1.2 μl of 200 mM dithiothreitol, 5 μl of 10 μM oligo(dT)-poly(A)(Boeringer Mannheim, 12–18 oligomer), 1 μl(1 μCi) of ³H-TTP(thymidinetriphosphate) and 23.6 μl of water; and the resulting mixture was kept at 37° C. After 1 hour, the mixture was poured onto a WHATMAN DEB1 filter and the filter was washed three times with 5 ml of 2×SSC buffer solution(17.53 g of sodium chloride, 8.82 g of sodium citrate, pH 7.0, 1 liter of water) for about 10 minutes each time, and twice with 95% ethanol for 10 seconds. The filter was put on aluminium foil and dried with an infra-red lamp. The amount of radioactivity was counted using a liquid scintillation counter. IC$_{50}$ of each compound was determined by measuring the concentration of the inhibitor that can reduce the activity of the reverse transcriptase by 50%.

To determine the cytotoxicity of the compound of the present invention, 0.1 μM to 100 μM of the compound was added to H9 cell or sup T1 cell and the mixture was cultured on a rpmi-1640 medium at 37° C. The medium was refreshed every 3 days and the extent of cell proliferation was observed using Hemacytometer according to the trypan blue dye exclusion technique which is well known in the art. CT$_{50}$(i.e., the concentration at which 50% of the cells die) was determined.

The measured IC$_{50}$ and CT$_{50}$ of the compound of the present invention are 15 nM and 10,000 nM, respectively, whereas MK-639 has IC$_{50}$ of 10 nM and CT$_{50}$ of 10,000 nM and ABI-538 of Abott Co. has IC$_{50}$ of 53 nM and CT$_{50}$ of 10,000 nM.

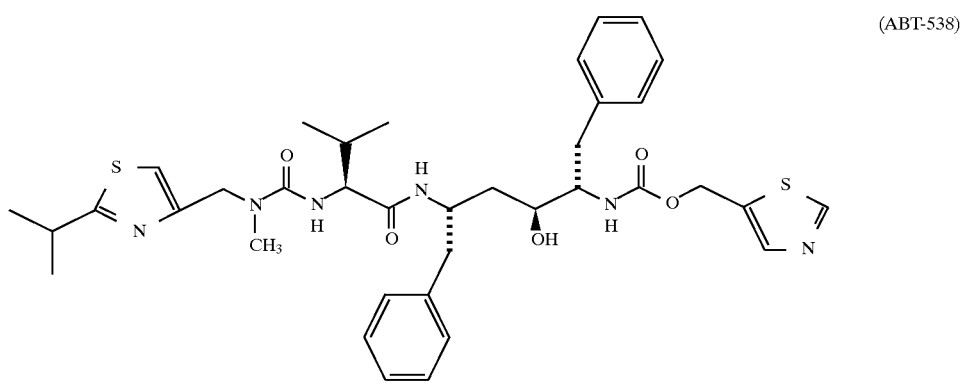

(ABT-538)

As can be seen from the above results, the compound of the formula(I) of the present invention is an excellent HIV protease inhibitor which has a high inhibition activity and low cytotoxicity.

While the invention has been described with respect to the specific embodiments, it should be recognized that various modifications and changes may be made by those skilled in the art to the invention which also fall within the scope of the invention as defined by the appended claims.

What is claimed is:

1. A cis-epoxide compound of formula (I) and pharmaceutically acceptable salts, hydrates and solvates thereof:

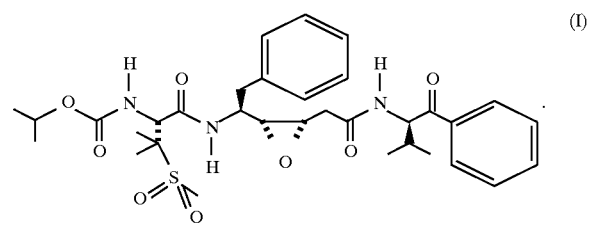

(I)

2. A process for preparing the compound of formula (I) according to claim 1 which comprises:

coupling a compound of formula (II) with a compound of formula (III) to obtain a compound of formula (VI);

epoxidizing the compound of formula (VI) to obtain a compound of formula (V);

removing the benzyloxycarbonyl protecting group from the compound of formula (V) to obtain an amine compound; and coupling the amine compound with a compound of formula (VI):

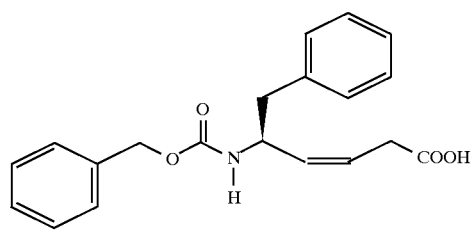
(II)
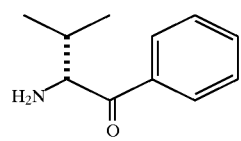
(III)
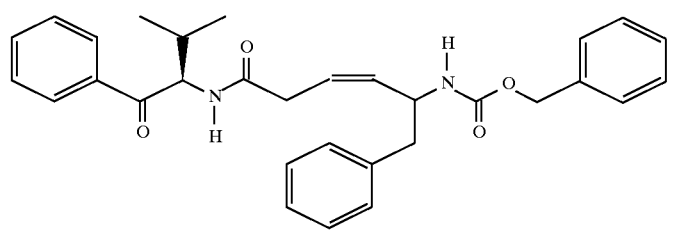
(IV)
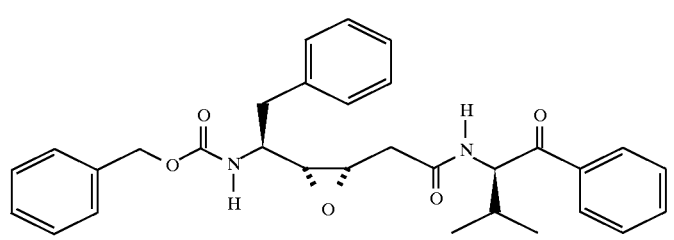
(V)
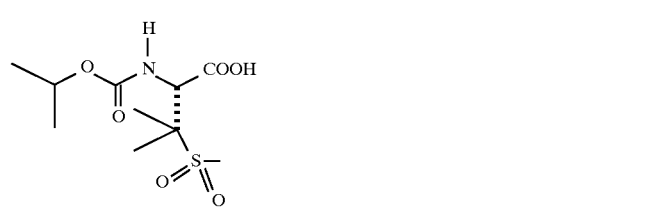
(VI)
3. A pharmaceutical composition for treating or preventing diseases caused by HIV infection comprising a therapeutically effective amount of the compound of claim 1 and a pharmaceutically acceptable carrier.
* * * * *